(12) United States Patent
Hansmann et al.

(10) Patent No.: US 9,841,336 B2
(45) Date of Patent: Dec. 12, 2017

(54) PRESSURE SENSOR, MEASURING DEVICE, REACTION CARRIER AND MEASURING METHOD

(71) Applicant: Dräger Safety AG & Co. KGaA, Lübeck (DE)

(72) Inventors: Hans-Ullrich Hansmann, Barnitz (DE); Philipp Rostalski, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 0 days.

(21) Appl. No.: 14/896,765

(22) PCT Filed: May 20, 2014

(86) PCT No.: PCT/EP2014/001350
§ 371 (c)(1),
(2) Date: Dec. 8, 2015

(87) PCT Pub. No.: WO2014/194982
PCT Pub. Date: Dec. 11, 2014

(65) Prior Publication Data
US 2016/0138988 A1 May 19, 2016

(30) Foreign Application Priority Data
Jun. 8, 2013 (DE) .......... 10 2013 009 641

(51) Int. Cl.
*G08B 21/00* (2006.01)
*G01L 9/00* (2006.01)
(Continued)

(52) U.S. Cl.
CPC ............ *G01L 9/00* (2013.01); *B01J 19/0093* (2013.01); *G01L 9/0001* (2013.01);
(Continued)

(58) Field of Classification Search
CPC combination set(s) only.
See application file for complete search history.

(56) References Cited

U.S. PATENT DOCUMENTS

| | | |
|---|---|---|
| 4,287,750 A | 9/1981 | Eckstein et al. |
| 5,089,232 A * | 2/1992 | May .................... G01N 21/783 |
| | | 422/404 |

(Continued)

FOREIGN PATENT DOCUMENTS

| | | |
|---|---|---|
| DE | 28 43 651 A1 | 4/1980 |
| DE | 10 2004 036214 A1 | 2/2006 |

(Continued)

OTHER PUBLICATIONS

"Dräger-Röhrchen & CMS—Handbuch 16. Auflage", Feb. 1, 2011, p. 2, 39, 70-105, 394, 395, XP055133367, Retrieved from Internet [on Aug. 5, 2014]: http://www.draeger.com/sites/assets/PublishingImages/Segments/Industrie/Dokumente/roehrchen_handbuch_br_9092084_de.pdf, pp. 72-74.

*Primary Examiner* — Travis Hunnings
(74) *Attorney, Agent, or Firm* — McGlew and Tuttle, P.C.

(57) ABSTRACT

A pressure sensor (100) for a measuring system (10) measuring concentrations of gaseous and/or aerosol components of a gas mixture with a reaction carrier (14), with a flow channel (42). The flow channel (42) forms a reaction chamber (46) with a reactant (48), that enters into an optically detectable reaction, and with a measuring device (12) with a gas port unit (5) connecting an inlet channel (16) and an outlet channel (18) to the flow channel (42) and a gas delivery unit (28). The pressure sensor (100) measures a pressure difference of a gas mixture flowing through the gas delivery assembly unit (2) and/or the flow channel (42) of the reaction carrier (14) and has an elastic element (102), which is configured to undergo deformation as a function of
(Continued)

the pressure difference. A measuring method, a measuring device and a reaction carrier for such a measuring system are also provided.

17 Claims, 8 Drawing Sheets

(51) Int. Cl.
  *G01L 19/00* (2006.01)
  *G01M 3/28* (2006.01)
  *G01N 31/22* (2006.01)
  *G08B 21/18* (2006.01)
  *B01J 19/00* (2006.01)

(52) U.S. Cl.
  CPC ........ *G01L 9/0077* (2013.01); *G01L 19/0023* (2013.01); *G01M 3/2846* (2013.01); *G01N 31/223* (2013.01); *G08B 21/182* (2013.01); *B01J 2219/0093* (2013.01); *B01J 2219/0097* (2013.01); *B01J 2219/00783* (2013.01); *B01J 2219/00831* (2013.01); *B01J 2219/00833* (2013.01); *B01J 2219/00837* (2013.01); *B01J 2219/00963* (2013.01); *B01J 2219/00972* (2013.01); *B01J 2219/00986* (2013.01); *B01J 2219/00988* (2013.01)

(56) References Cited

U.S. PATENT DOCUMENTS

| 6,817,311 | B1* | 11/2004 | Treen ..................... A63B 41/00 116/268 |
| 2006/0150385 | A1 | 7/2006 | Gilligan et al. |
| 2009/0064790 | A1* | 3/2009 | Davidovits .......... B01J 19/0093 73/718 |
| 2010/0326803 | A1* | 12/2010 | Um ..................... H03K 17/9629 200/312 |

FOREIGN PATENT DOCUMENTS

| DE | 10 2010 035 728 A1 | 3/2012 |
| DE | 10 2012 014 504 A1 | 1/2014 |
| EP | 1 818 664 A1 | 8/2007 |

* cited by examiner

PRESSURE SENSOR, MEASURING DEVICE, REACTION CARRIER AND MEASURING METHOD

CROSS REFERENCE TO RELATED APPLICATIONS

This application is a U.S. National Phase Application of International Application PCT/EP2014/001350 filed May 20, 2014 and claims the benefit of priority under 35 U.S.C. §119 of German Patent Application 10 2013 009 641.3 filed Jun. 8, 2013 the entire contents of which are incorporated herein by reference.

FIELD OF THE INVENTION

The present invention pertains to a pressure sensor for a measuring system for measuring a concentration of gaseous and/or aerosol components of a gas mixture by means of a reactant, which is designed to enter into an optically detectable reaction with a component of the gas mixture, which component is to be measured, or with a reaction product of the component to be measured. The present invention pertains, furthermore, to a reaction carrier and to a measuring method for such a measuring system.

BACKGROUND OF THE INVENTION

Gas detector tubes, which are filled with a reactant, which enters into an optically detectable reaction with a certain chemical compound, are known from the state of the art. A defined quantity of a gas mixture is pumped through the gas detector tube, for example, with a hand pump. A concentration of the chemical compound to be measured is then determined by means of a change in the color of the reactant.

In addition, so-called chip-based measuring systems are known, in which the reactant is provided in a plurality of reaction chambers, which are arranged on a reaction carrier and which can be used each for a measurement. The reaction carrier can be inserted into a measuring device, which detects the reaction carrier and carries out a corresponding measuring method for measuring a concentration of the corresponding component of the gas mixture. A function test of the measuring system is necessary to rule out malfunction in case of measurements in which no concentration is measured because the component to be measured is not present in the gas mixture or is present in the gas mixture below a detection threshold only.

SUMMARY OF THE INVENTION

An object of the present invention is to provide a simple sensor system for such a measuring system and a corresponding measuring method.

The present invention pertains to a pressure sensor for a measuring system for measuring a concentration of gaseous and/or aerosol components of a gas mixture with a reaction carrier, which has at least one flow channel, said flow channel forming a reaction chamber with a reactant, which is designed to enter into an optically detectable reaction with at least one component to be measured in the gas mixture or with a reaction product of the component to be measured. and with a measuring device, which comprises a gas port assembly unit for connecting a gas inlet channel and a gas outlet channel to the flow channel of the reaction carrier and a gas delivery device for delivering the gas mixture through the flow channel of the reaction carrier. The pressure sensor is configured to measure a pressure difference of a gas mixture flowing through the gas delivery assembly unit and/or flow channel of the reaction carrier and has an elastic element, which is configured to undergo deformation as a function of the pressure difference. This makes possible a simple and compact as well as lightweight mode of construction of a pressure sensor for a measuring system, which is especially advantageous for portable mobile measuring systems.

The pressure sensor is arranged, for example, in the measuring system and is configured to measure the pressure of the gas flowing through the gas delivery assembly unit and/or flow channel of the reaction carrier against an ambient pressure. This makes possible a simple mode of construction of the pressure sensor with minimal diminishing of the flow through the flow channel and the gas port assembly unit.

As an alternative, the pressure sensor is arranged in the measuring system and is configured to measure the pressure of the gas flowing through the gas port assembly unit of the measuring device and/or the flow channel of the reaction carrier as a pressure drop over a restriction in the flow. In this way, the pressure sensor can be arranged flexibly in the measuring system at any desired point in the gas port assembly unit or the flow channel.

The pressure sensor preferably comprises an optical display element, which is configured to be detected by an optical sensor of the measuring device. No complex separate sensor system is necessary in this way for determining the pressure, because the pressure sensor can advantageously be arranged and designed such that a simultaneous detection of the optically detectable reaction is possible by a common optical sensor.

The optical display element may be embodied by a change in brightness, contrast and/or color, by a movable component, for example, an indicator or by a combination thereof. The optical sensor is preferably a color sensor, which makes it possible to distinguish different colors, and the optical display element comprises a color code, and the colors of the optical display element, which are detected by the color sensor, change with a change in the pressure difference.

The elastic element is formed, for example, by a diffusely reflecting, transparent membrane, and a contact surface is provided, which is configured such that the membrane comes into contact with increasing area percentages on the contact surface as a function of increasing pressure difference, and the area percentages that are in contact with the contact surface are optically distinguishable from the area percentages of the membrane that are not in contact with the contact surface. This makes possible a simple determination of different pressure differences by the optical sensor. In particular, a color distinction is also possible due to contact surfaces having different colors.

It is also possible that a window is provided, which is arranged to be detected by the optical sensor, and a display body is provided, which is increasingly visible in the window with increasing pressure difference as a function of the pressure difference.

Furthermore, the elastic element may be designed as a volume element, which changes its volume as a function of the pressure difference and performs an optically detectable translatory or rotary motion as a function of the change in volume.

As an alternative, the pressure sensor may comprise an electric or magnetic measuring element, which detects an electric capacity or a magnetic conductivity as a function of the deformation of the elastic element. The pressure difference can be carried out in this way via a measurement of the electric capacity or magnetic conductivity.

The present invention pertains, furthermore to a measuring device for a measuring system for measuring a concentration of gaseous and/or aerosol components of a gas mixture with a reaction carrier, which has at least one flow channel, wherein said flow channel forms a reaction chamber with a reactant, which is designed to enter into an optically detectable reaction with at least one component to be measured in the gas mixture or with a reaction product of the component to be measured. The measuring device comprises a gas port assembly unit for connecting a gas inlet channel and a gas outlet channel to the flow channel of the reaction carrier, a gas delivery device for delivering the gas mixture through the flow channel of the reaction carrier and a pressure sensor according to the invention, wherein the pressure sensor is provided at the gas port assembly unit and preferably at a gas port of the gas delivery assembly unit for connection to the flow channel of the reaction carrier. The pressure difference can be measured in this way in the gas delivery assembly unit and, for example, a check can be performed for leakage flows. The pressure sensor is preferably provided at the downstream-side gas port.

The present invention pertains, furthermore, to a reaction carrier for a measuring system for measuring a concentration of gaseous and/or aerosol components of a gas mixture with a measuring device, which comprises a gas port assembly unit for connecting a gas inlet channel and a gas outlet channel to a flow channel of the reaction carrier and a gas delivery device for delivering the gas mixture through the flow channel of the reaction carrier. The reaction carrier has at least one flow channel, said flow channel forming a reaction chamber with a reactant, which is designed to enter into an optically detectable reaction with at least one component to be measured in the gas mixture or with a reaction product of the component to be measured. The reaction carrier comprises at least one above-described pressure sensor, said pressure sensor being formed at the at least one flow channel (42). The pressure sensor is not arranged in this way at the reusable measuring device but at the replaceable reaction carrier. Since a flow channel is usually used only once or a few times, a simple mode of construction of the pressure sensor is possible, because the pressure sensor is not exposed in this way to many different chemicals over a long time. The pressure sensor is preferably provided on the downstream side, in a port element of the reaction carrier.

It is also possible that the elastic element of the pressure sensor is provided in a transparent section of the flow channel and/or of the gas delivery assembly unit and performs an optically detectable translatory or rotary motion as a function of the pressure difference.

The present invention pertains, furthermore, to a measuring method for a measuring system for measuring a concentration of gaseous and/or aerosol components of a gas mixture with a reaction carrier, which has at least one flow channel, said flow channel forming a reaction chamber with a reactant, which is designed to enter into an optically detectable reaction with at least one component to be measured in the gas mixture or with a reaction product of the component to be measured, and with a measuring device. The measuring method comprises the method steps of measuring a reference pressure difference in a gas port assembly unit of the measuring device or in a flow channel of the reaction carrier against the ambient pressure or over a restriction in the flow, of delivering a gas flow through the flow channel of the reaction carrier and of measuring a pressure difference in a gas port assembly unit of the measuring device or in a flow channel of the reaction carrier against the ambient pressure or over a restriction in the flow during the delivery of the gas flow through the flow channel.

The above-described embodiments may be combined with one another and with the above-described aspects as desired in order to achieve advantages according to the present invention. Further features and advantages of the present invention appear from the embodiments described below The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
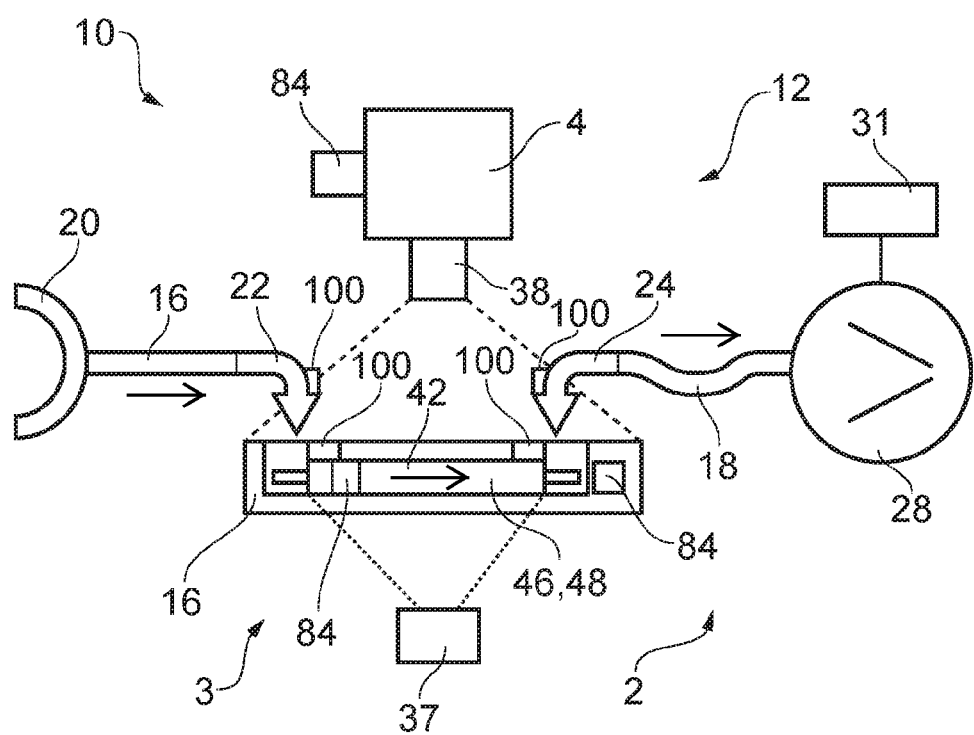
FIG. 1 is a schematic view of a first embodiment of a measuring system according to the present invention with a measuring device and with a reaction carrier according to the present invention.

FIG. 1 shows a schematic view of a gas-measuring system, hereinafter also called measuring system 10. The measuring system 10 comprises a measuring device 12 and a reaction carrier 14. The reaction carrier 14 has at least one flow channel 42, which forms a reaction chamber 46 with a reactant 48. The reactant 48 is designed to enter into an optically detectable reaction with at least one component to be measured in a gas mixture or with a reaction product of the component to be measured. In this way, the component to be measured can enter into a reaction with the reactant either directly, or an intermediate reaction may be provided, in which the component to be measured enters into a reaction with an intermediate reactant and the reaction product formed in the process will then enter into the optically detectable reaction with the reactant.

The measuring device 12 comprises a gas delivery assembly unit 2 with a gas delivery device 28 for delivering the gas mixture through the flow channel 42 of the reaction carrier 14.

The gas delivery assembly unit 2 comprises, furthermore, a gas inlet channel 16 with a gas mixture inflow opening 20, through which the gas mixture can flow into the gas inlet channel 16, and a gas port 22, which may be connected to the flow channel 42 of the reaction carrier 14.

The gas delivery assembly unit 2 comprises, furthermore, a gas outlet channel 18 with a gas port 24, which may be connected to the flow channel 42 of the reaction carrier 14. The gas delivery device 28 is arranged in the gas outlet channel 18 and makes possible the delivery of the gas mixture in a direction of flow indicated by arrows in FIG. 1. The gas-carrying components of the gas delivery assembly unit 2, especially the gas ports 22, 24, and the gas inlet channel 16, form a gas port assembly unit 5.

A control/regulating unit 31 is provided, which is configured to control or regulate the flow of the gas mixture through the flow channel as a function of at least one reaction rate parameter. Reaction rate parameters may be, for example, the speed of propagation of a reaction front of the optically detectable reaction or a temperature of the gas mixture flowing through the flow channel 42. Temperature-measuring elements 84, which makes possible a measurement of the temperature of the gas mixture directly in the flow channel 42 of the reaction carrier 14 or indirectly via a measurement of the temperature of the reaction carrier 14 and/or of the measuring device 12, are provided for measuring the temperature of the gas mixture flowing through the flow channel 42.

The measuring device 12 comprises, moreover, a detection assembly unit 3 with an illuminating device 37 for illuminating the reaction chamber 46 of the reaction carrier 14. The illuminating device 37 is configured in the embodiment being shown to illuminate the reaction chamber with a broad-band spectrum. The broad-band spectrum corresponds, for example, to white light. However, adjacent spectral ranges, as well as infrared spectral ranges or ultraviolet spectral ranges may also be covered by the broad-band spectrum.

The detection assembly unit 3 comprises, furthermore, an optical sensor 38 for detecting the optically detectable reaction in the reaction chamber 46 of the reaction carrier 14, as well as an analysis unit 4 for analyzing the data of the optically detectable reaction, which data are detected by the optical sensor, and for determining a concentration of the component of the gas mixture.

The optical sensor 38 is a multichannel sensor, which can detect a plurality of color channels. The optical sensor 38 is configured as a digital camera in the embodiment being shown and will hereinafter also be called digital camera 38.

The analysis unit 4 is configured to perform a weighting of the color channels during the analysis of the data of the optical sensor 38.

The illuminating device 37 is arranged in FIG. 1 on the side of the reaction carrier 14 located opposite the optical sensor 38 for the sake of clarity. However, the illuminating device may be arranged in different positions at the measuring device 12 and make possible a corresponding illumination. For example, the illumination and the observation through the optical sensor 38 may take place from the same direction and hence on the same side of the reaction carrier 14.

The detection assembly unit 3 comprises, furthermore, an analysis unit 4, which is configured to determine the concentration of the component to be measured in the gas mixture exclusively from parameters of the reaction front that can be determined optically. For example, the speed of the front and an intensity gradient of the reaction front propagating in the reaction chamber 46 in the direction of flow are measured for this during the detection of a reaction front propagating in the reaction chamber 46 and the concentration of the component to be measured is determined from it.

However, in case the gas mixture does not contain the component to be measured or said component is present below a detection threshold, a function test of the measuring system 10 must be performed in order to rule out a measuring error based on a malfunction of the measuring system, for example, based on a leak or a clogging of the flow channel.

Pressure sensors 100, which are arranged each at the two gas ports 22, 24 and at a flow channel 42 with the reaction chamber 46 at port elements 44 located on both sides, are provided for the function test. However, it is also possible that, for example, only one pressure sensor 100 is arranged at one of the two gas ports 22, 24 or at the flow channel 42 of the reaction carrier 14.

The pressure sensors 100 are arranged each in the field of view of the optical sensor 38 indicated by broken lines and can thus be detected optically and analyzed. No complex separate sensor system is necessary in this way for detecting the pressure, and the pressure sensors can have a simple design.

In the embodiment being shown, the field of view of the optical sensor 38 covers essentially the entire width of the reaction carrier. It is, however, also possible that the field of view of the optical sensor detects only certain areas of the reaction carrier, for example, only the right-hand, downstream-side half of the reaction carrier. The pressure sensors 100 are arranged correspondingly in this area in this case.

Figure 2:
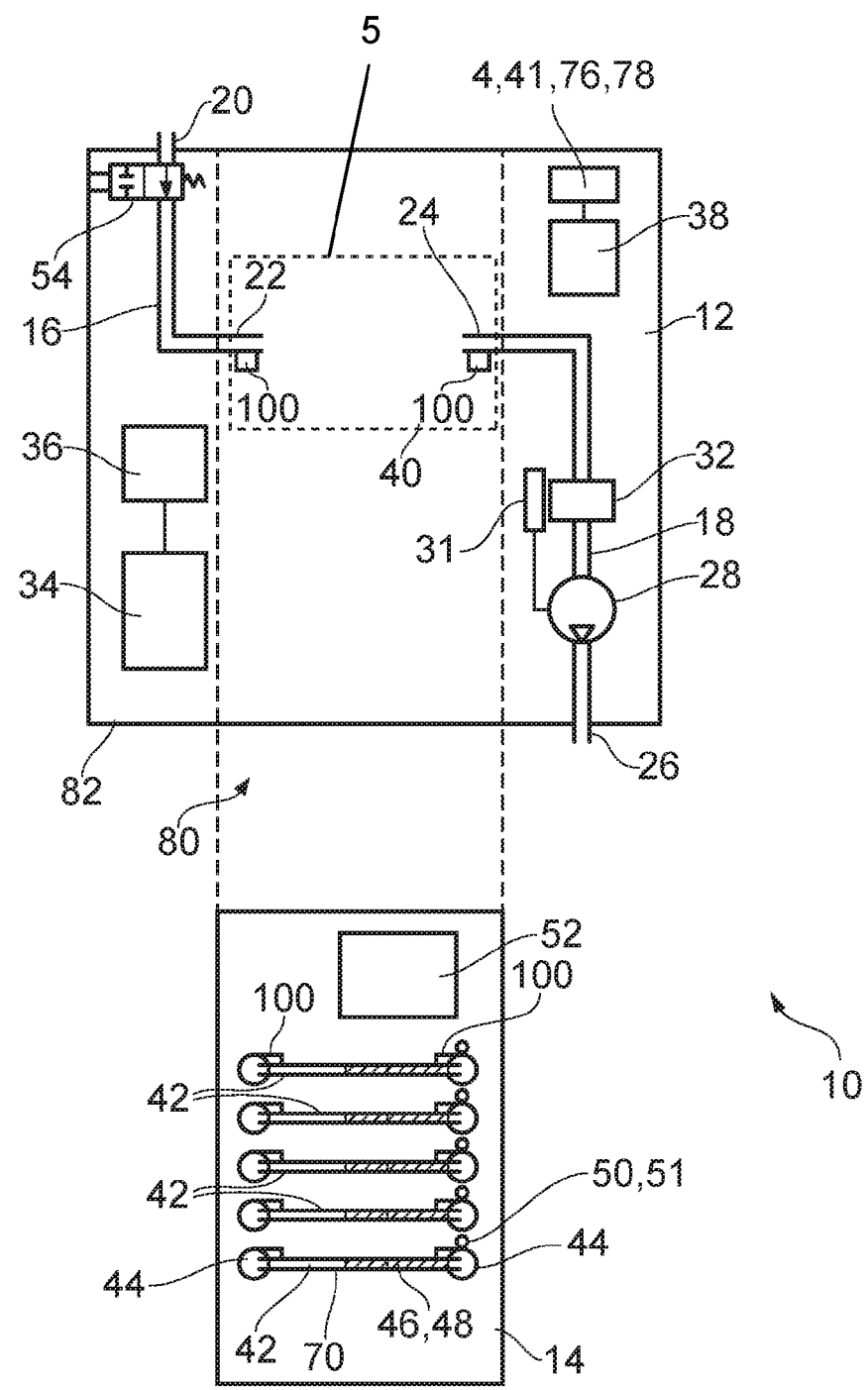
FIG. 2 is a detailed view of the measuring system from FIG. 1.
Figure 3:
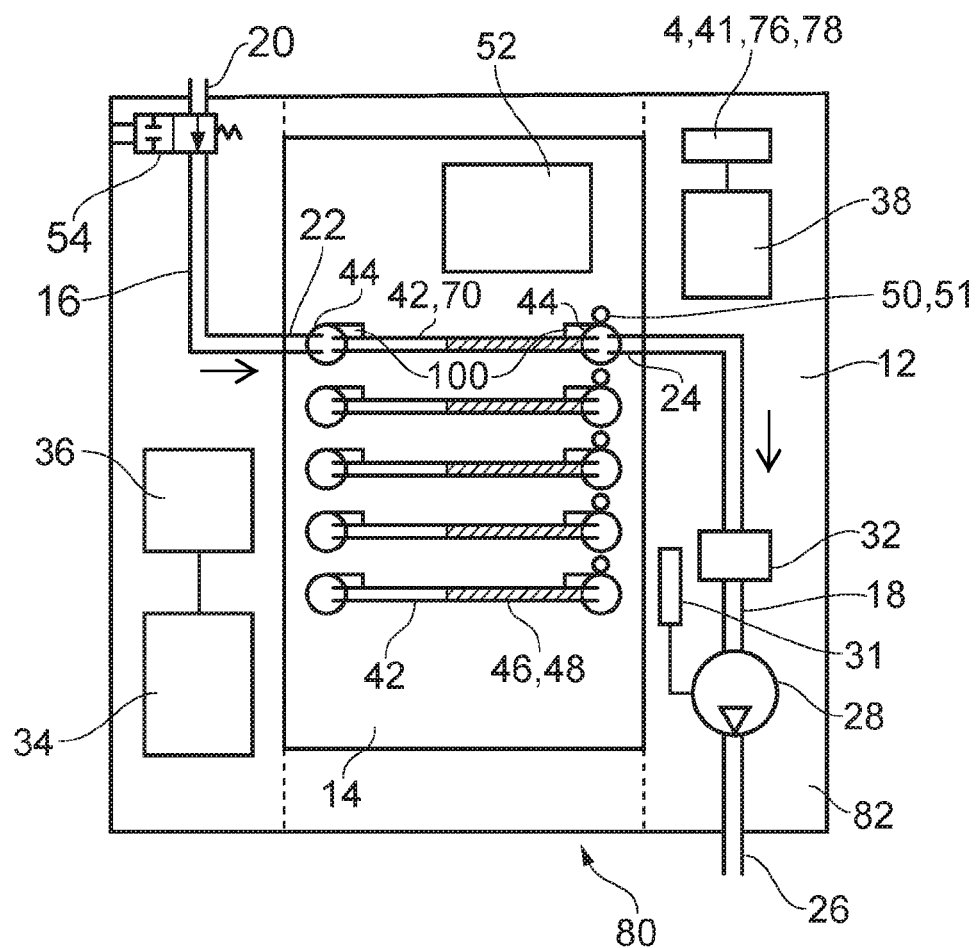
FIG. 3 is a detailed view of the measuring system from FIG. 1 with the reaction carrier inserted.

FIGS. 2 and 3 show a more detailed view of the measuring system 10 for measuring or detecting the concentration of gaseous and/or aerosol components. A replaceable reaction carrier 14, also called reaction carrier unit, is inserted manually by hand by a user into the measuring device 12, also called gas-measuring arrangement or other gas-measuring system. The measuring system 10 or the measuring device 12 is a small, portable device, which can be used as a mobile device and is provided with a battery as a power source. FIG. 2 shows the measuring device 12 and the reaction carrier 14 separately and FIG. 3 shows the measuring device 12 with the reaction carrier 14 inserted into it.

The gas delivery device 28, which is embodied by a pump designed as a suction pump, is arranged at a housing of the measuring device 12. The housing forms, besides, a mount, especially a sliding mount, for the displaceable reaction carrier 14. The reaction carrier can be moved within the housing of the measuring device by means of a reaction carrier delivery device 34 with a motor, e.g., an electric motor designed as a servomotor and with a gear mechanism that can be rotated by the servomotor, because there is a mechanical contact or a connection between the drive roller and the reaction carrier.

The measuring system 10 comprises the measuring device 12 and at least one reaction carrier 14. The gas inlet channel 16 extends from the gas mixture inflow opening 20 to the first gas port 22. The gas outlet channel 18 extends from the second gas port 24 to a gas mixture outflow opening 26.

The gas inlet channel 16 is made of glass, as a result of which a chemical reaction or the deposit of gaseous components on the wall of the gas inflow channel is prevented or reduced.

A valve 54 is arranged at the gas mixture inflow opening 20 upstream of the gas inlet channel 16. The valve makes possible a gas flow through the gas inlet opening 16 in its first position, shown, and prevents a gas flow through the gas inlet channel 16 in a second position. The valve 54 is configured as a 2/2-way valve in the embodiment shown.

However, it is also possible that the measuring device 12 is configured without a valve 54 at the gas mixture inflow opening 20. The number of components through which the gas mixture flows in front of the reaction chamber 46 can be reduced in this manner and a chemical reaction or the deposit of gaseous components on the components can thus be prevented or reduced.

Further, a buffer 32, which makes possible a uniform gas flow through the gas outlet channel 18, is arranged in the gas outlet channel 18.

The measuring device 12 comprises, in addition, a reaction carrier delivery device 34, which makes possible a motion of the reaction carrier 14 relative to the gas inlet channel 16 and the gas outlet channel 18.

A position sensor 36 is used to detect a relative position of the reaction carrier 14 and the gas ports 22, 24.

The optical sensor 38 for detecting an optically detectable reaction is provided in the form of a digital camera 38 and makes it possible to record the recording field 40, which is indicated by the rectangle drawn in dotted line in FIG. 1.

A central control unit 38 is provided, which can process the data detected by the optical sensor and controls the measuring method. In the embodiment being shown, the central control unit comprises the analysis unit 4.

The reaction carrier 14 has a plurality of flow channels 42, which extend each between two port elements 44. In the embodiment being shown, each of the flow channels 42 forms a reaction chamber 46, which is filled with reactant 48. The reactant 48 is a chemical compound, which enters into an optically detectable reaction with a gaseous and/or aerosol component of a gas mixture. This is, for example, a colorimetric reaction.

In the embodiment being shown, the flow channels 42 are each filled with the reactant 48 on their right side. Another gas treatment element, for example, a drying substance, is provided on the left side of the flow channels 42.

A display pin 50, which forms a code 51, is associated with each flow channel 42, said code 51 being detected by the position sensor 36 and makes possible an independent positioning of the reaction carrier 14 in respective relative positions associated with the flow channels 42. Another type of code 51, for example, an electric, electronic or magnetic code, which can be detected by a corresponding position sensor 36, may be provided as well. However, an optical code 51 is preferably provided at least additionally in order for the user of the measuring system 10 to be able to determine by viewing the reaction carrier 14 at a glance whether the reaction carrier still has unused reaction chambers.

The reaction carrier 14 has, further, an information field 52, on which information is stored. The information field 52 is configured in the embodiment being shown as an optical information field, on which information is stored, which can be read by the digital camera 38. As an alternative, the information field 52 may be provided as an electronic memory for information and designed, for example, as an RFID chip or SROM chip, which can be read and/or written to in a wireless manner or via electric contacts.

The recording field of the digital camera 38 is configured in the embodiment being shown such that the reaction chambers 46, the display pins 50, and the information field 52 are detected by the digital camera 38 in at least one respective relative position of the reaction carrier 14 in the measuring device 12. The digital camera 38 can be used in this way to detect the optically detectable reaction of the reactant 48 in the reaction chambers 46 of the reaction carrier 14, on the one hand, and to read the information in the information field 52 and as a position sensor 36 for detecting the relative position of the reaction carrier and the gas ports 22, 24, on the other hand. It is, however, also possible that the position sensor 36 and a reading device for reading the information field 52 are designed as one device or as two separate devices.

A function test of the measuring system 10, especially in case the gas mixture does not contain the component to be measured or this component is present below a detection threshold, in which test a pressure difference in the flow channel 42 and/or in the gas port assembly unit 5 can be measured especially optically by the pressure sensors 100, will be described below.

Figure 4:
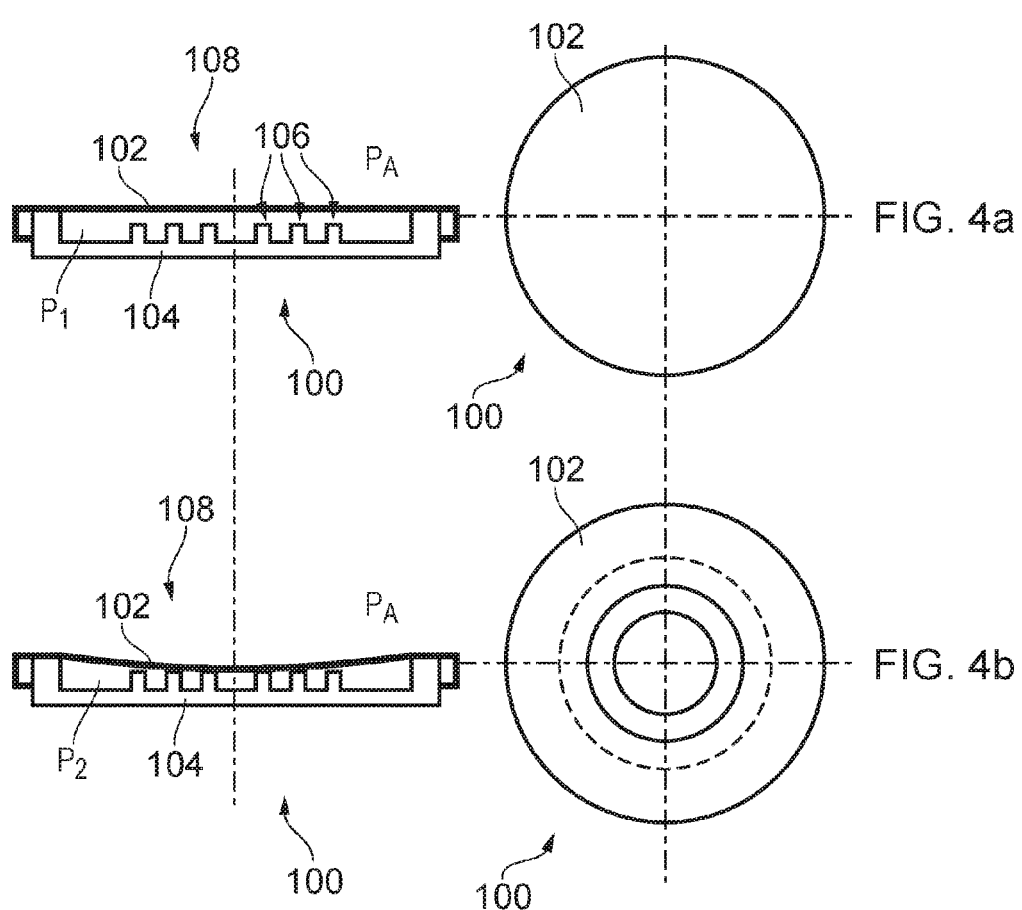
FIG. 4a is a pressure sensor according to a first embodiment in a sectional view and in a top view for a first pressure difference.
FIG. 4b is the pressure sensor from FIG. 4a in a sectional view and a top for a second pressure difference.

FIGS. 4a and 4b show a pressure sensor 100 according to a first embodiment in a sectional view on the left side and in a top view on the right side. The pressure sensor 100 is configured to measure a pressure difference of a gas mixture flowing through the gas port assembly unit 5 of the measuring device 12 and/or the flow channel 42 of the reaction carrier 14. The pressure sensor 100 has an elastic element 102, which is configured to undergo deformation as a function of the pressure difference.

The first embodiment shows a pressure sensor 100, which is configured to measure a pressure difference between an internal pressure P1 or P2 within the gas port assembly unit 5 or the flow channel 42 and an ambient pressure PA. The pressure sensor 100 has a fixed sensor housing 104, which forms with the elastic element 102 in the form of a membrane an interior space, which is connected to the gas-carrying spaces of the gas port assembly unit 5 or with the flow channel 42 or is part of these. Furthermore, the sensor housing 104 forms contact surfaces 106.

FIG. 4a shows the sensor at pressure difference at which the internal pressure essentially corresponds to the ambient pressure and the elastic element 102 is essentially in a relaxed central position. The elastic element 102 is located at a spaced location from the contact surfaces 106 of the sensor housing 104 in this central position. The membrane of the elastic element 102 is configured as a diffusely reflecting, transparent membrane, so that only a contiguous area of diffusely reflected light can be seen in the top view of the sensor in the central position of the membrane.

FIG. 4b shows, by contrast, the pressure sensor 100 at a pressure difference at which a vacuum prevails in the interior space of the pressure sensor 100 relative to the ambient pressure. The elastic element is pulled to the contact surfaces 106 in this case and increasing area percentages will come into contact with the contact surface with increasing pressure difference, and the area percentages that are in contact with the contact surface can be optically distinguished from the area percentages that are not in contact.

In case of the pressure difference shown in FIG. 4b, the elastic element 102 is fully in contact with the inner two of the three ring-shaped contact surfaces 106 and has a short distance from the outer ring-shaped contact surface 106. The surface areas that are in contact with the two inner contact surfaces 106 can thus be seen in the top view by dark rings, because no light or only a smaller percentage of light is reflected by the membrane on these area percentages. The area percentages on which the elastic element 102 comes into contact can be detected by the digital camera 38, and a corresponding pressure difference can be determined. The number of visible rings is an indicator of the pressure difference in the embodiment being shown. The elastic element 102 thus forms, together with the contact surfaces 106, an optical display element 108, which is configured to be detected by the optical sensor in the form of the digital camera 38 of the measuring device 12.

The contact surfaces 106 are preferably marked by color, for example, by rings having different colors in this embodiment, and thus they form a color code, so that the color information detected by the camera 38 is an indicator of the pressure difference, the different rings becoming visible in different colors with increasing pressure difference.

The pressure sensor 100 according to the first embodiment may be formed, for example, in a simple manner directly at the flow channel 42 of the reaction carrier, the analysis and processing of the measurement results by the measuring device being possible by means of the digital camera 38. The pressure sensor 10 can thus be provided on the reaction carrier 14 in a simple manner and cost-effective manner with a compact design.

Figure 5:
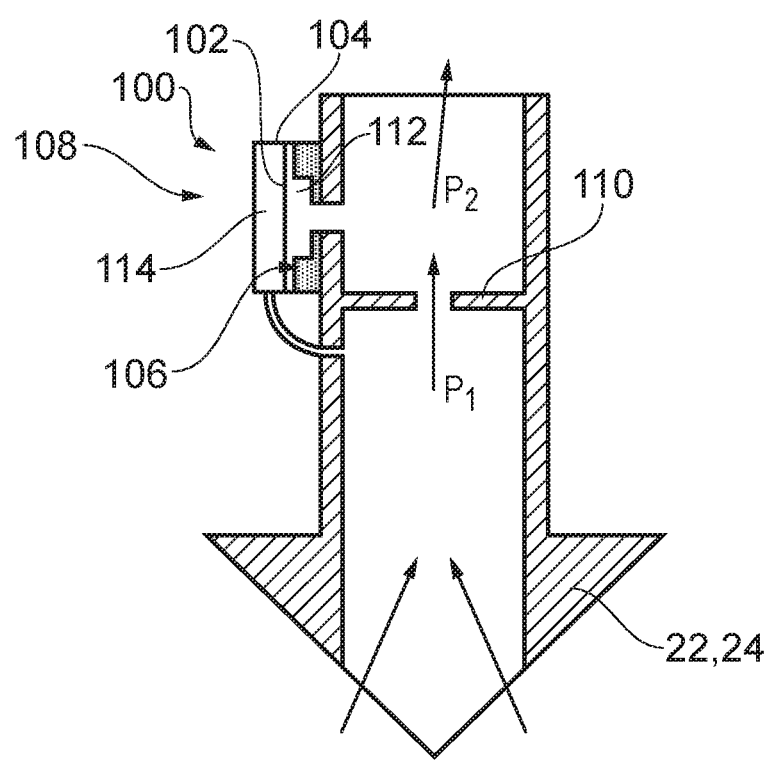
FIG. 5 is a pressure sensor according to a second embodiment in a sectional view.

FIG. 5 shows a second embodiment of a pressure sensor 100. The pressure sensor 100 is arranged at a gas port 22 or 24. As an alternative, the pressure sensor 100 may also be arranged, as described above, at another location in the measuring system.

Contrary to the pressure sensor 100 according to the first embodiment, the pressure sensor 100 from FIG. 5 measures a differential pressure over a restriction 110 within the gas-carrying channel of the gas port 22, 24, a pressure P1 being present in front of the restriction and a pressure P2 being present after the restriction.

The pressure sensor 100 has a sensor housing 104, in which a first chamber and a second chamber 112, 114, respectively, are formed, which are separated by an elastic element 102 in the form of a membrane, which is configured analogously to the previous embodiment.

The first chamber 112 is connected to the gas-carrying channel of the gas port 22, 24 downstream of the restriction 110, while the second chamber 114 is connected to the gas-carrying channel of the gas port 22, 24 upstream of the restriction 110. In the first chamber 112, the sensor housing 104 forms a ring-shaped contact surface 106, with which the elastic element 102 comes into contact at a corresponding pressure difference. The elastic element 102 and the contact surface 106 thus form an optical display element 108, analogously to the previous embodiment.

The sensor housing is made transparent in the area of the second chamber 114 in order to guarantee that the optical display element 108 is located in the field of view of the digital camera 38.

Figure 6:
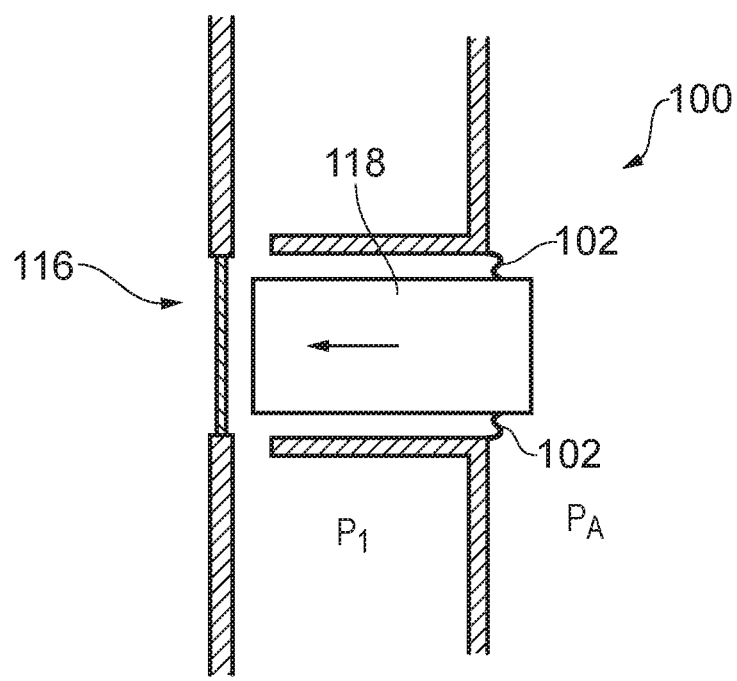
FIG. 6 is a pressure sensor according to a third embodiment in a sectional view.

FIG. 6 shows a third embodiment of a pressure sensor 100. A transparent window 116 is provided in the wall of a gas-carrying channel, for example, in the flow channel 42 of the reaction carrier 14 or in a channel of the gas port assembly unit 5. An optical display element 108 is formed by a display body 118, which is mounted movably and is increasingly visible in the window 116 with increasing pressure difference as a function of the pressure difference. It is also possible that the entire channel is made transparent and the entire channel thus forms the window 116. The display body 118 must be arranged in this case such that its position can be unambiguously detected optically as a function of the pressure difference.

The display body 118 is connected to a wall of the channel via the elastic element 102. The display body 118 thus sees the ambient pressure PA on one side and the internal pressure P1 on the other side. The display body 118 is increasingly pulled against the spring force of the elastic element 102 into the channel and thus becomes increasingly visible through the window 116 as the vacuum increases.

Figure 7:
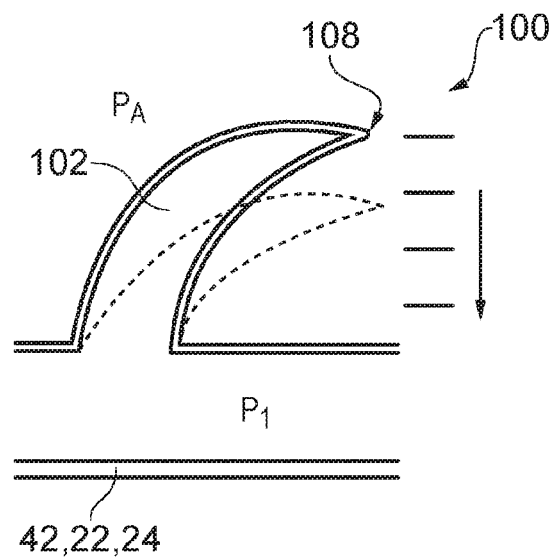
FIG. 7 is a pressure sensor according to a fourth embodiment in a sectional view.
Figure 8:
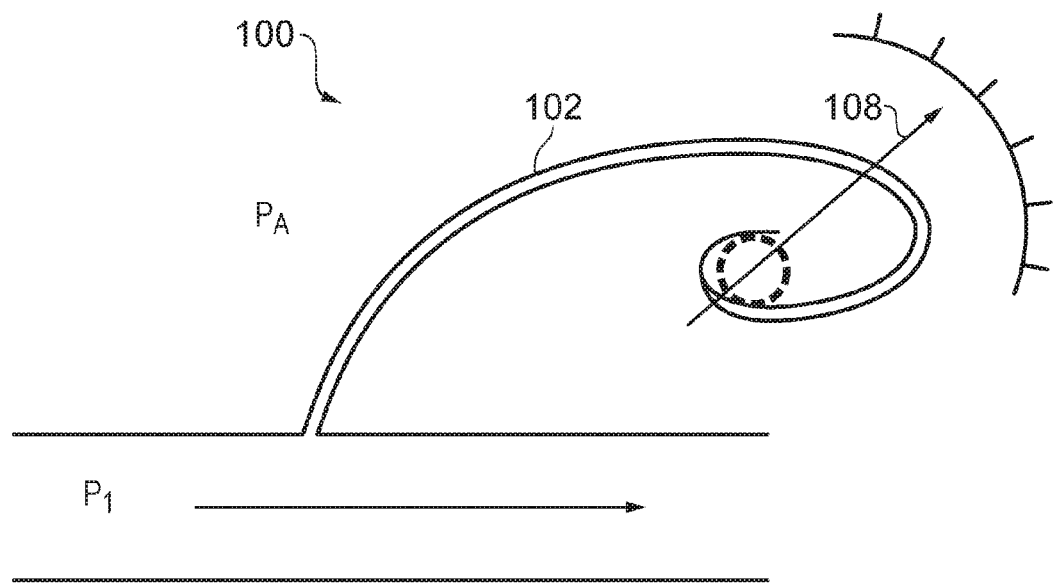
FIG. 8 is a pressure sensor according to a fifth embodiment in a sectional view.

FIGS. 7 and 8 show each a pressure sensor 100 with an elastic element 102, which is configured as a volume element and changes its volume as a function of the pressure difference between the internal pressure P1 and the ambient pressure PA.

In the fourth embodiment in FIG. 7, the elastic element 102 is a sickle-shaped volume element, which performs a translatory motion as a function of the change in volume, and the tip of the sickle-shaped elastic element 102 moves in the direction of the arrow shown with increasing vacuum P1 relative to the ambient pressure PA. The pressure difference can be determined by means of a scale or a comparison image.

In the fifth embodiment in FIG. 8, the elastic element 102 is a spiral volume element, which performs a rotary motion as function of the change in volume, and the center of the spiral elastic element 102 rotates about the spiral axis as the vacuum P1 increases relative to the ambient pressure PA. An indicator is fastened as an optical display element at the center of the spiral element 102. The pressure difference can be determined by means of a scale or a comparison image and the rotary motion.

Figure 9:
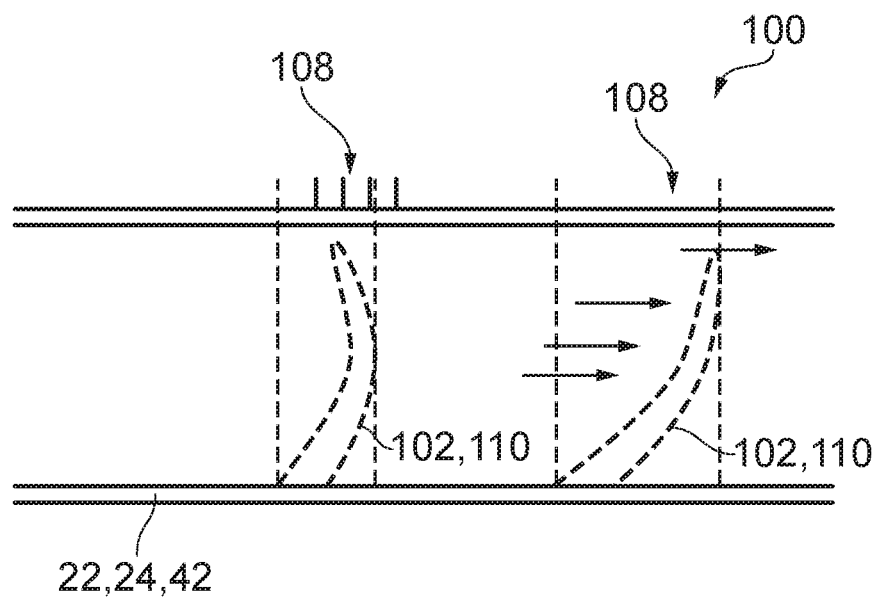
FIG. 9 is a pressure sensor according to a sixth embodiment in a sectional view.

FIG. 9 shows a sixth embodiment of a pressure sensor 100, in which the pressure sensor is formed by an elastic element 102 within a transparent, gas-carrying channel of the flow channel 42 or of the gas port assembly unit 5, which elastic element 102 forms a restriction 110 for the gas flow itself. The elastic element 102 is sickle-shaped and is shown in a relaxed central position on the left side of FIG. 9, in which no flow is being delivered through the channel and the pressure difference over the restriction 110 formed by the elastic element 102 is correspondingly essentially zero. In the relaxed central position, the elastic element extends essentially at right angles to the direction of flow, and the tip of the sickle-shaped elastic element is arranged at a first position at the channel wall.

The elastic element 102 is shown on the right side of FIG. 9 in case of a gas flow through the channel, and a pressure difference develops over the restriction 110 and the elastic element is deformed. The tip of the elastic element 102 moves in the direction of the flow, on the one hand, and the motion of the tip can be determined by a scale or a comparison image and can be used as an indicator of the pressure difference. On the other hand, the elastic element is deformed such that the width of the elastic element increases with increasing deformation when viewed from the top. The elastic element 102 is preferably marked in color, so that the width of the elastic element forms an optical display element 108, which is detected by the digital camera 38 and is analyzed for determining the pressure difference.

In the embodiments shown, the pressure sensors 100 can always be read via the optical sensor 38 of the measuring device. It is, however, also possible that the pressure sensors 100 comprise electric or magnetic measuring elements, which detect an electric conductivity, an electric capacity or a magnetic conductivity as a function of the deformation of the elastic element. For example, the membrane of the elastic element 102 according to the first and second embodiments may have a conductive coating in order to form an electric contact (and the conductivity of said contact) or a variable capacity (due to variable distance or variable area) with contact surfaces 106 of the sensor housing 104, which have correspondingly conductive coatings.

The detection of the magnetic conductivity may be effected by induction. The magnetic resistance may be embodied as a coil or as a massive material with high electric conductivity. The magnetic fields induced by a permanently installed coil are attenuated by the eddy currents, which are induced in the coil or the massive material, depending on the distance and the area. The energy removed can be measured in an oscillatory circuit and from the reduced resonance step-up resulting from the energy. The magnetic conductivity can be measured by means of the magnetic coupling in case of materials with high permeability. The membrane to be measured is arranged in an air gap of a magnetic circuit and can be measured, for example, by means of a Hall sensor as a modified function of the current intensity relative to the field strength or directly as the field strength in case of permanent magnets.

A measuring method will be described below with reference to FIGS. 2 and 3.

The reaction carrier 14 is inserted into an insertion opening 80 in a housing 82 of the measuring device 12. The reaction carrier 14 is inserted manually into the insertion opening, grasped by the reaction carrier delivery device 34 and transported forward into the insertion direction.

When transporting the reaction carrier 14, the information field 52 of the reaction carrier 14 passes through the recording field 40 of the digital camera 38, while the information on the information field 52 can be detected by the digital camera 38 and analyzed in an analysis device of the central control unit 41. It is also possible that the reaction carrier is positioned in a reading position, in which reading of the information field 52 is made possible. The information is stored optically on the information field 52 in the embodiment being shown and thus it can be read by the digital camera 38 in a simple manner. It is also possible, as an alternative, that an electronic information field 52 is provided, which is configured, for example, as an active or passive RFID chip or SRAM chip, and can be read in a wireless manner or via electric contacts. The electric contacts are preferably made of a current-carrying material via data lines to the inlet and outlet openings of the flow channels 42 and gas pipe branches, so that a current and data connection is established between the SRAM chip and a corresponding reading device, while the gas pipe branches are located in the inlet and outlet openings.

The information of the reaction carrier 14 contained on the information field 52, especially in reference to the component to be measured in the gas mixture and a corresponding concentration range, is read in a first method step.

The reaction carrier 14 is then positioned in a relative position in relation to the gas ports 22, 24 of the measuring device 12, and a flow channel 42, which has an unused reaction chamber 46, namely, the first flow channel 42 of the reaction carrier 14 in the insertion direction in the example shown in FIG. 3, is selected.

A connection is established between the gas ports 22, 24 through the second flow channel 42.

A reference image of the flow channel 42 is recorded before the start-up of the gas delivery device 28, and the pressure sensors 100 at the reaction carrier 14 and at the gas port assembly unit 5 are in the field of view of the digital camera 38. An instantaneous pressure ratio can be measured, on the one hand, from the recorded image. On the other hand, the recorded image can be used for a comparison with images recorded during the delivery of the gas mixture.

After the reference image is recorded, the gas delivery device 28 delivers a gas mixture to be measured through the outlet channel 18, the second flow channel 42 and the gas inlet channel 16, and the digital camera 38 detects a possible optically detectable reaction in the reaction chamber 46.

The digital camera 38 records a flow image of the flow channel 42 during the delivery of the gas mixture through the gas delivery device 28. This flow image can be used, for example, both for the optical detection of the pressure sensors 100 and for the detection of the optically detectable reaction.

The control unit 108 analyzes the reference image and the flow image of the digital camera 38 and determines the pressure differences at the positions of the pressure sensors 100 by means of the optical display elements 108 detected. It can be checked in this way whether the gas delivery device 28 is delivering a gas flow through the flow channel 42 or the gas port assembly unit 5.

The digital camera 38 preferably records flow images of the flow channel 42 continuously in order to make possible a continuous optical detection of the pressure differences and of the optically detectable reaction.

The detection assembly unit 3 detects a reaction front propagating in the direction of flow in the reaction chamber 46 and the speed thereof during the delivery of the gas mixture and determines a preliminary measurement result for the concentration of the component to be measured in the gas mixture from the speed of the reaction front.

A final measurement result for the concentration of the component of the gas mixture is determined and outputted after the end of delivery of the gas mixture.

If the component to be determined in the gas mixture is not contained in the gas mixture or it is present at a concentration below the detection threshold of the concentration range of the reaction carrier 14 present, no optically detectable reaction is detected in the reaction chamber 46, and no reaction front will consequently develop in the reaction chamber 46.

A corresponding result of the measurement is displayed by the measuring device, for example, optically or acoustically.

A check is preferably performed for leakage flows each time a connection is established between the gas ports 22, 24 via a flow channel 42.

In a first step, the gas port 24 of the gas outlet channel 18 is connected to the corresponding port element 44 of the reaction carrier 14. Gas is delivered in a second step through the gas outlet channel 18 and the flow channel 42 of the reaction carrier 14, which said flow channel 42 is connected to said gas outlet channel 18, and the pressure difference against the ambient pressure or a pressure difference over a restriction 110 and hence a gas flow through the gas outlet channel is measured by the pressure sensors 100. If the system comprising the gas outlet channel and the flow channel is gas-tight, a corresponding vacuum as well as essentially no gas flow through the gas outlet channel 18 are measured, because the flow channel 42 of the reaction carrier 14 is closed in a gas-tight manner via the second port element 44 closed by the sealing device 62.

In a further step, the gas inlet channel 16 is closed upstream by the valve 54 and the gas port 22 of the gas inlet channel 16 is connected to the corresponding port element 44 of the reaction carrier 14. Gas is subsequently delivered by the gas delivery device 28 through the gas outlet channel 18, the flow channel 42 and the gas inlet channel 16, and the pressure differences are again measured analogously at the positions of the pressure sensors 100 to check for leakage flows. If the system comprising the gas outlet channel 18, the flow channel 42 and the gas inlet channel 16 is gas-tight, a corresponding vacuum as well as essentially no gas flow through the gas outlet channel 18 are measured, because the gas inlet channel 16 is closed in a gas-tight manner by the valve 54.

The fact that no gas flow is essentially measured in the measurement described in the previous paragraphs in case of a gas-tight measuring system 10, in which normal pressure is present in the gas outlet channel 18, the flow channel 42 and/or the gas inlet channel 16 before the checking for the leakage flows shall be interpreted such that an essentially exponentially decreasing gas flow that follows the vacuum is measured. In other words, the measured gas flow corresponds in a gas-tight measuring system 10 to the quantity of gas present in the channels 16, 18, 42 at the beginning of the measurement, which is pumped out by the gas delivery device 28 during the checking for the leakage flows.

If a leakage flow, i.e., a gas flow exceeding the gas flow mentioned in the previous paragraph, is measured through the gas outlet channel 18 at the time of the checking, a corresponding error message is sent by the measuring device 12. The flow channel 42 on the reaction carrier 14 or the gas outlet channel 18 and the gas inlet channel 16 of the measuring device 12 can then be checked, for example, by the user.

It is also possible that both gas ports 22, 24 of the gas outlet channel 18 and of the gas inlet channel 16 are already connected to the corresponding port elements 44 of the flow channel 42 in a first step and a single check is correspondingly performed for leakage flows.

While specific embodiments of the invention have been shown and described in detail to illustrate the application of the principles of the invention, it will be understood that the invention may be embodied otherwise without departing from such principles.

The invention claimed is:

1. A pressure sensor for a measuring system for measuring a concentration of gaseous and/or aerosol components of a gas mixture, the pressure sensor comprising:
   a reaction carrier, which has at least one flow channel, wherein the flow channel forms a reaction chamber with a reactant, which is configured to enter into an optically detectable reaction with a component to be measured in the gas mixture or with a reaction product of the component to be measured; and
   a measuring device, the measuring device comprising a gas port assembly unit for connecting a gas inlet channel and a gas outlet channel to the flow channel of the reaction carrier and a gas delivery device for delivering the gas mixture through the flow channel of the reaction carrier, the pressure sensor being configured to measure a pressure difference of a gas mixture flowing at least one of through the gas delivery assembly unit and the flow channel of the reaction carrier and the pressure sensor has an elastic element, which is configured to undergo deformation as a function of the pressure difference, wherein the pressure sensor further comprises an optical display element, which comprises the elastic element, wherein the optical display element is configured to be detected by an optical sensor of the measuring device, wherein the optical display element is formed and arranged to be simultaneously detected with the optically detectable reaction by the optical sensor.

2. A pressure sensor in accordance with claim 1, wherein the elastic element comprises a diffusely reflecting, transparent membrane and the optical display element further comprises a contact surface configured such that the membrane will come into contact with the contact surface over increasing area percentages as a function of increasing pressure difference, wherein the area percentages in contact with the contact surface can be optically distinguished from the area percentages of the membrane not in contact.

3. A pressure sensor in accordance with claim 1, further comprising:
   a window, which is arranged to be detected by an optical sensor of the measuring device; and
   a display body, which is increasingly visible in the window with increasing pressure difference as a function of the pressure difference.

4. A pressure sensor in accordance with claim 1, wherein the elastic element is configured as a volume element, which changes its volume as a function of the pressure difference and performs an optically detectable translatory or rotary motion as a function of the change in volume, the gas port assembly unit comprising a gas outlet port and a gas inlet port, the gas outlet port being connected to the gas inlet channel, the gas inlet port being connected to the gas outlet channel, the gas inlet port, the gas outlet port and the at least one gas channel being in fluid communication with each other when the reaction carrier is inserted in the measuring device.

5. A pressure sensor in accordance with claim 1, further comprising an elastic or magnetic measuring element, which detects an electric conductivity, an electric capacity or a magnetic conductivity as a function of the deformation of the elastic element, the measuring device comprising the gas inlet channel and the gas outlet channel, the gas inlet channel being arranged on one side of the at least one channel and the gas outlet channel being arranged on another side of the at least one channel when the reaction carrier is inserted in a reaction carrier receiving area of the measuring device, wherein the gas inlet channel is connected to the gas outlet channel via at least the at least one channel when the reaction carrier is inserted in the reaction carrier receiving area.

6. A measuring device for a measuring system for measuring a concentration of gaseous and/or aerosol components of a gas mixture, the measuring device comprising:
   a reaction carrier, which has at least one flow channel, wherein the flow channel forms a reaction chamber with a reactant, which is configured to enter into an optically detectable reaction with a component to be measured in the gas mixture or with a reaction product of the component to be measured;
   a gas port assembly unit for connecting a gas inlet channel and a gas outlet channel to the flow channel of the reaction carrier;
   a gas delivery device for delivering the gas mixture through the flow channel of the reaction carrier;
   an optical sensor; and
   a pressure sensor provided at the gas port assembly unit, the pressure sensor comprising an elastic element configured to undergo deformation as a function of the pressure difference, the pressure sensor being configured to detect a pressure difference of a gas mixture flowing at least one of through the gas delivery assembly unit and the flow channel of the reaction carrier, wherein the pressure sensor further comprises an optical display element, which comprises the elastic element, the optical sensor being configured to detect simultaneously the optical display element and the optically detectable reaction.

7. A measuring device in accordance with claim 6, wherein the elastic element comprises a diffusely reflecting, transparent membrane and the optical display element further comprises a contact surface configured such that the membrane will come into contact with the contact surface over increasing area percentages as a function of increasing pressure difference, wherein the area percentages in contact with the contact surface can be optically distinguished from the area percentages of the membrane not in contact.

8. A measuring device in accordance with claim 6, further comprising an optical sensor wherein the pressure sensor further comprises:
 a window arranged to be detected by the optical sensor; and
 a display body, which is increasingly visible in the window with increasing pressure difference as a function of the pressure difference.

9. A measuring device in accordance with claim 6, wherein the elastic element is configured as a volume element, which changes its volume as a function of the pressure difference and performs an optically detectable translatory or rotary motion as a function of the change in volume, the gas port assembly unit comprising a gas output port and a gas input port for connecting the gas inlet channel and the gas outlet channel to the flow channel of the reaction carrier, the gas output port being located at a spaced location from the gas input port, the gas output port and the gas input port extending in a direction transverse to an insertion direction of the reaction carrier, the gas outlet port and the gas inlet port being parallel to the at least one flow channel.

10. A measuring device in accordance with claim 6, the pressure sensor further comprises an elastic or magnetic measuring element, which detects an electric conductivity, an electric capacity or a magnetic conductivity as a function of the deformation of the elastic element.

11. A reaction carrier for a measuring system for measuring a concentration of gaseous and/or aerosol components of a gas mixture with a measuring device, the reaction carrier comprising:
 at least one flow channel, wherein the measuring device comprises a gas port assembly unit for connecting a gas inlet channel and a gas outlet channel to the at least one flow channel of the reaction carrier and a gas delivery device for delivering the gas mixture through the flow channel of the reaction carrier, wherein the flow channel forms a reaction chamber with a reactant, which is configured to enter into an optically detectable reaction with at least one component to be measured in the gas mixture or with a reaction product of the component to be measured; and
 at least one pressure sensor at the at least one flow channel, wherein the pressure sensor comprises an optical display element, which comprises an elastic element, wherein the optical display element is configured to be detected by an optical sensor of the measuring device, wherein the optical display element is formed and arranged to be simultaneously detected with the optically detectable reaction by the optical sensor.

12. A reaction carrier in accordance with claim 11, wherein the gas outlet port and the gas inlet port are parallel to the at least one flow channel.

13. A reaction carrier in accordance with claim 11, wherein the pressure sensor further comprises:
 a window arranged to be detected by the optical sensor of the measuring device; and
 a display body, which is increasingly visible in the window with increasing pressure difference as a function of the pressure difference.

14. A reaction carrier in accordance with claim 11, wherein the elastic element is configured as a volume element, which changes its volume as a function of the pressure difference and performs an optically detectable translatory or rotary motion as a function of the change in volume, the gas port assembly unit comprising a gas outlet port and a gas inlet port for connecting the gas inlet channel and the gas outlet channel of the measuring device to the at least one flow channel of the reaction carrier, one end of the flow channel being aligned with the gas outlet port and another end of the flow channel being aligned with the gas inlet port when the reaction carrier is inserted in a reaction carrier receiving area of the measuring device.

15. A reaction carrier in accordance with claim 11, wherein the pressure sensor further comprises an elastic or magnetic measuring element, which detects an electric conductivity, an electric capacity or a magnetic conductivity as a function of the deformation of the elastic element.

16. A measuring method for a measuring system for measuring a concentration of gaseous and/or aerosol components of a gas mixture with a reaction carrier, which has at least one flow channel, wherein the flow channel forms a reaction chamber with a reactant, which is configured to enter into an optically detectable reaction with at least one component to be measured in the gas mixture or with a reaction product of the component to be measured, and with a measuring device, the method comprising the steps of:
 measuring a reference pressure difference in a gas port assembly unit of the measuring device or in a flow channel of the reaction carrier against the ambient pressure or over a restriction in the flow; and
 delivering a gas flow through the flow channel of the reaction carrier;
 measuring a pressure difference in a gas port assembly unit of the measuring device or in a flow channel of the reaction carrier against the ambient pressure or over a restriction in the flow via a pressure sensor, wherein the pressure sensor comprises an elastic element and an optical display element, the optical display element comprising the elastic element, wherein the optical display element is configured to be detected by an optical sensor of the measuring device, wherein the optical display element is formed and arranged to be simultaneously detected with the optically detectable reaction by the optical sensor.

17. A measuring method in accordance with claim 16, wherein the measuring device comprises a gas inlet port and a gas outlet port, the measuring method further comprising:
 moving the reaction carrier relative to the measuring device such that the at least one flow channel is in fluid communication with the first gas port and the second gas port.

* * * * *